United States Patent [19]

Poler

[11] 4,277,852
[45] Jul. 14, 1981

[54] INTRAOCULAR LENS WITH ASTIGMATISM CORRECTION

[76] Inventor: Stanley Poler, 78 E. Second St., New York, N.Y. 10003

[21] Appl. No.: 132,275

[22] Filed: Mar. 20, 1980

Related U.S. Application Data

[63] Continuation-in-part of Ser. No. 113,967, Jan. 21, 1980.

[51] Int. Cl.³ .............................. A61F 1/16; A61F 1/24
[52] U.S. Cl. ............................................................ 3/13
[58] Field of Search ............................................ 3/13, 1

[56] References Cited

U.S. PATENT DOCUMENTS

| | | | |
|---|---|---|---|
| 3,971,073 | 7/1976 | Richards et al. | 3/13 |
| 3,996,627 | 12/1976 | Deeg et al. | 3/13 |
| 4,079,470 | 3/1978 | Deeg et al. | 3/13 |
| 4,080,709 | 3/1978 | Poler | 3/13 |
| 4,087,866 | 5/1978 | Choyce et al. | 3/13 |
| 4,122,556 | 10/1978 | Poler | 3/13 |

FOREIGN PATENT DOCUMENTS 959314  3/1957  Fed. Rep. of Germany ................. 3/13

OTHER PUBLICATIONS

A Lens for All Seasons (Book) by Jerald L. Tennant, Aug. 1976, pp. 13-21.

Primary Examiner—Ronald L. Frinks
Attorney, Agent, or Firm—Hopgood, Calimafde, Kalil, Blaustein & Judlowe

[57] ABSTRACT

The invention contemplates an intraocular lens or the like which so combines an optically finished lens element with supporting mount or haptic structure that a given astigmatic correction incorporated in the finish of the lens is automatically implantable with correct optical orientation of the correction axis. The mount is characterized with an angularly unique recognizable haptic formation from which a unique ultimately implanted orientation can be recognized by the ophthalmological surgeon, and the prescription orientation of the astigmatic correction is, upon lens-to-haptic assembly, set in such predetermined angular relation to the angularly unique haptic formation that correct optical orientation of the implant is assured.

16 Claims, 7 Drawing Figures

INTRAOCULAR LENS WITH ASTIGMATISM CORRECTION

RELATED APPLICATION

This application is a continuation-in-part of my copending application, Ser. No. 113,967, filed Jan. 21, 1980.

BACKGROUND OF THE INVENTION

The invention relates to intraocular lenses, whether designed for anterior-chamber implantation or for posterior-chamber implantation in the human eye, and whether or not iris-supported.

As far as I am aware, with the exception of my constructions, prior intraocular lenses have been of plastic construction, and they are tissue-reactive in the sense that tissue growth after implantation is not retarded and can become a clouding factor to degrade optical performance of the implant. With such plastic lenses, sterilization must be accomplished using a caustic solution or ethylene oxide gas.* Such lenses are injection-molded products and therefore cannot be classed with the quality of an optically finished lens. But glass lenses as implants have been generally shunned, primarily because of the high specific gravity of glass, as compared to that of plastic; see Binkhorst, et al., "A Weightless Iseikonic Intraocular Lens", American Journal of Ophthalmology, Vol. 58, No. 1, July 1964, pp. 73 to 78. And, in particular, it is noted that although Choyce, et al., U.S. Pat. No. 4,087,866 mentions glass as a possible lens material, the disclosure is silent on any suggestion of optically finished glass for the purpose.

*A glass lens would allow for autoclaving. To my best knowledge and belief, the difficulties and expense of making molds for plastic intraocular lenses have meant that the implanted lens must be simple and basic, reliance being placed upon later prescription of corrective spectacles if astigmatism is to be corrected in an individual case.

BRIEF SUMMARY OF THE INVENTION

It is an object of the invention to provide an improved intraocular lens (with associated haptic structure) and a method of making the same.

It is a specific object to make such a lens using a single optically finished glass lens element, thus assuring high optical quality.

Another specific object is to make such a lens which incorporates a predetermined degree of astigmatism correction and which incorporates a unique angular orientation feature whereby the ophthalmological surgeon can recognize orientation and thus is enabled to correctly orient the astigmatism correction in the course of an implantation operation.

A general object is to meet the above objects with structure which is autoclavable, and which can be reliably manufactured in production quantities, at relatively low cost for the inherent high optical quality involved.

The foregoing and other objects and features of the invention are achieved in configurations wherein a circular optically finished glass lens element is so retained by haptic structure having a uniquely recognizable transverse axis that an astigmatism correction ground into the optical finish of the lens element may be at predetermined (prescription) angular relation to the uniquely recognizable orientation axis of the haptic structure, thus enabling the surgeon to make an optically correct implant which has built-in correction for an astigmatic defect.

DETAILED DESCRIPTION

The indicated feature is illustratively described for haptics of single and multiple-element varieties, in conjunction with the accompanying drawings, in which.

Figure 1:
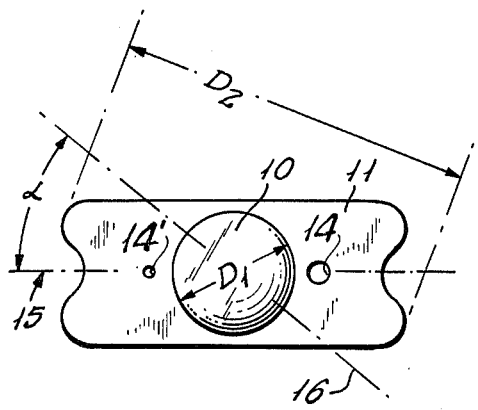
FIG. 1 is a plan view of an anterior-chamber lens and haptic of the invention.
Figure 2:
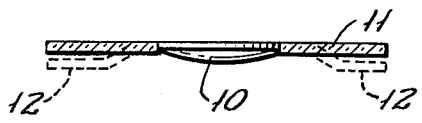
FIGS. 2 and 3 are longitudinal sectional views to show alternative forms of the lens and haptic of FIG. 1.
Figure 3:
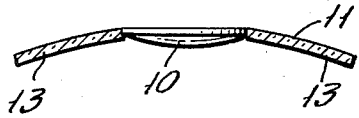

In the configuration of FIG. 1, an intraocular-lens assembly comprises a circular optically finished lens 10 of diameter $D_1$ secured centrally to an elongate haptic base 11 of thin flat glass sheet. The lens 10 may be plano-convex in which case one surface of the haptic base 11 may be in bonded intimate continuous adjacency to the plane side of lens 10. Alternatively, the base 11 may be centrally apertured to the peripheral contour of lens 10, with lens 10 peripherally bonded therein, as shown in FIGS. 2 and 3. The sheet 11 is of width essentially determined by the lens diameter and extends longitudinally beyond diametrically opposite regions of the lens, but its maximum longitudinal extent is short of the mounting diameter $D_2$ dictated by inner confines of the anterior chamber of an eye, at the so-called "angle", namely the groove or space between the scleral ridge and the iris. The diametral span $D_2$ varies and is generally 12 to 14 mm, depending on the size of the eye, and it is important for avoidance of trauma that the span $D_2$ of the haptic be selected correctly, within the indicated range. Means whereby the span $D_2$ of the haptic may be adjustably selected are disclosed in said copending application but are not important to the present invention and are therefore not here described.

The indicated securing of lens 10 to haptic 11 is preferably achieved by fusing the two elements using a suitable frit. Alternatively, one may employ an optical cement, inert to body fluids, such cement being selected from commercially available varieties, including sodium silicate, balsam compounds, benign epoxies, and UV-cured optical cements. Preferably, the longitudinal ends of haptic 11 are of smoothly undulated contour (as shown in FIG. 1) and are also offset axially in one direction away from the plane of support of lens element 10, thereby enabling an implanted lens element 10 to be clear of contact with the iris of the eye. In the event of fusing lens 10 to haptic 11, such offsets may be produced by slumping at the time of fusing, it being shown in FIG. 2 that for a haptic 11 that is flat at its central region of lens support, the slumping produces axially offset foot elements, suggested by phantom outlines 12; alternatively, in FIG. 3, the haptic 11 is arcuately bowed to produce the desired offset, with outer foot formations 13 extending in a single plane at the offset location. Still further, it will be understood that in the FIG. 2 or in the FIG. 3 situation, the haptic may be slumped to desired offsetting profile prior to or after the fused assembly of lens element 10 thereto.

For an all-glass structure of the described nature, the haptic 11 is typically about a quarter-millimeter thick, and the lens element 10 is of 5 mm diameter ($D_1$) and of maximum thickness approximating 0.3 mm. The indicated preference for fusing the parts not only assures bonding of a structure which is exclusively glass, but it (fusing) so heats the parts as to round (smouth out) all edges. The completed structure thus represents best chances for successful implantation, and for utmost resistance to post-operative tissue growth, as well as assured sterilization by autoclaving.

It is noted that the haptic 11 is of easily recognized elongated proportions, unique to an elongation axis 15 which is transverse to and passes through the optical axis of lens element 10. The surgeon will make his implant with the elongation axis 15 in a particular orientation (for example, vertical) and so the axis 15 provides a readily recognizable orientation reference, while large and small manipulating apertures 14–14', on the axis 15 and on opposite sides of lens 10, enable the surgeon to resolve as between the 6 o'clock and the 12 o'clock direction of the recognizable orientation. In accordance with the invention, this resolvable reference is utilized in assembling an astigmatism-corrected lens element 10 to the haptic 11.

Astigmatism-correction may be embodied in the optical finishing of lens element 10 by suitable grinding techniques involving a secondary eccentric grinding operation which is optically identifiable in terms of a unique transverse directional orientation, namely an orientation direction which extends diametrically through the optical axis of lens element 10 and which is angularly identified with respect to the resolvable reference. For any particular patient, there will be (a) a given magnitude or degree and (b) a given transverse-directional orientation of necessary correction for his astigmatism. The magnitude or degree of such correction is obtained by controlled eccentricity in the optical finishing of the lens element. But the transverse-directional orientation of the correction is obtained by first identifying the transverse directionality in the finished lens, and by then so angularly orienting this transverse directionality with respect to the reference axis 15 that prescription orientation is assured when implanted. In FIG. 1, an illustrative patient's prescribed transverse axis of astigmatism correction is identified at 16, namely, at an angle $\alpha$ to the reference axis 15. Therefore, once having optically identified the transverse directionality of eccentricity in the finished lens, and by orienting this transverse directionality with the alignment 16, the prescription is matched to the reference 15, so that upon the surgeon's implanting the assembly according to his intended orientation (for example, with axis 15 vertical), the patient will have been correctly fitted, in terms of the prescription axis of astigmatism correction.

Figure 4:
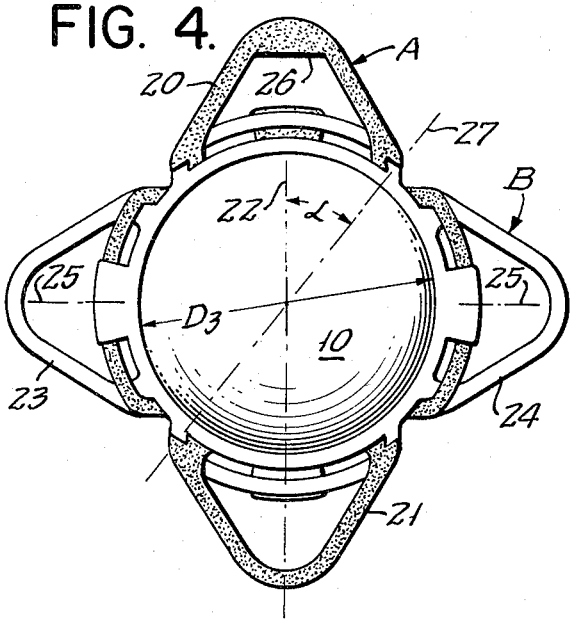
FIG. 4 is a plan view, to an enlarged scale, to show application of the invention to a two-piece haptic construction.

FIG. 4 illustrates that the invention is also applicable to intraocular-lens structures involving a two-piece haptic, as of the variety described in greater detail in my U.S. Pat. No. 4,122,556. The haptic of FIG. 4 comprises two almost-identical parts A–B, each of which is preferably fabricated by photographically delineated chemical or ion-bombardment milling techniques applied to thin autoclavable plastic sheet material, as in the manner described in detail in my U.S. Pat. No. 4,080,709. For convenience of recognition in FIG. 4, the part A is shown with stippled shading, and the part B is not shaded. Each of parts A–B has an annular body of inner diameter $D_3$ which, being less than the lens-element diameter $D_2$, circumferentially continuously laps a different one of the axial sides of the peripheral rim of lens element 10. Within their respective body annuli, and radially outside the periphery of lens element 10, the bodies of parts A and B have diametrically opposed sets of arcuate slots and pairs of hook formations, the patterns of parts A and B being in 90°-displaced relation, with the hook formations of the body of part A being engaged to the slot formations of part B, and vice versa. Diametrically opposite radially outward leg formations 20–21 span the respective opposed pairs of hook formations of part A (in a first predominant transverse direction 22) and diametrically opposite radially outward leg formations 23–24 span the respective opposed pairs of hook formations of part B (in a second predominant transverse direction 25). An integral chordal fillet 26 in leg 20 establishes uniqueness of the directional axis 22, so that the transverse direction 27 of astigmatism correction can be built into the completed assembly at prescription offset $\alpha$, upon appropriate angular orientation of lens element 10 with respect to the reference direction 22.

Figure 5:
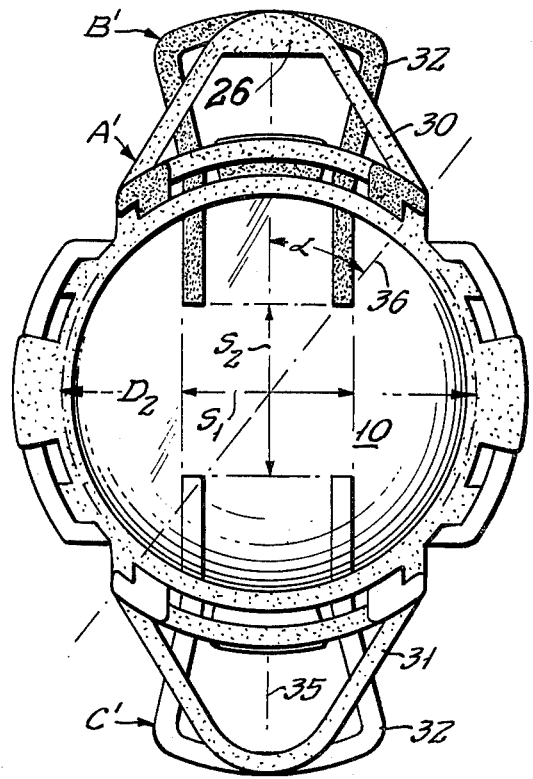
FIG. 5 is a view similar to FIG. 4, to show application of the invention to a three-piece haptic construction.
Figure 6:
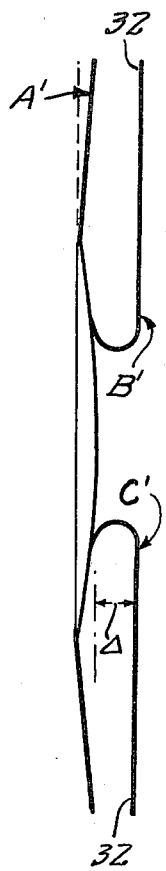
FIG. 6 is a side-elevation view of the construction of FIG. 5.
Figure 7:
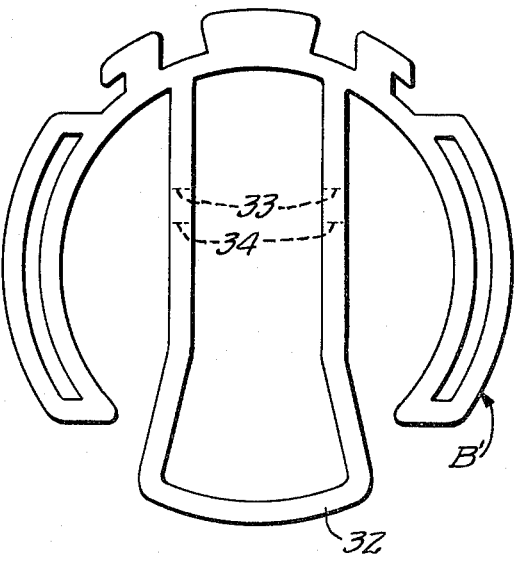
FIG. 7 is a plan view of one of the haptic pieces of the construction of FIG. 5.

FIGS. 5, 6 and 7 provide similar illustration of the invention in the context of a three-piece haptic, as of the variety shown in greater detail in my copending patent application, Ser. No. 100,243, filed Dec. 4, 1979. The three pieces of the haptic of FIGS. 5 and 6 comprise an annular-body part A' having two diametrically opposite radially outwardly extending stabilizing-foot formations 30–31, generally as described for part B of FIG. 4, and assembled in peripheral overlap with one axial side (the anterior side) of the rim of lens element 10. The second and third parts B'–C' of the haptic are duplicates of the part B' shown in FIG. 7, assembled to the opposite axial side (the posterior side) of the rim of lens element 10, being connected to each other and to part A' via hook-and-slot annular-body connections analogous to those of FIG. 4. Again, for convenience, shading has been adopted to enable ready differentiation of the haptic parts, part A' being in a medium stippled shading, part B' being in a darker stippled shading, and part C' being unshaded. As in said application Ser. No. 100,243, each of the parts B'–C' integrally includes an elongate looped stabilizing formation 32 permanently bent or crimped at spaced locations 33–34 whereby a trans-iris axial offset $\Delta$ is established for ultimate location of radially outward feet 32 to lightly resiliently engage features of the posterior chamber of the eye, while retaining lens element 10 and the haptic part A' in stabilized contact with the anterior side of the iris. By specifying the location of crimps 33–34, the surgeon may tailor the radially outward extent of the posterior feet 32 appropriate to the patient's posterior-chamber dimensions, and in any case, the trans-iris portion between crimps 33–34 may be at such relatively small limits of span $S_1$–$S_2$ as to present little or no limitation on normal iris action in response to changes in ambient light intensity.

The lens assembly of FIG. 5 will be seen to have a predominant and unique transverse identification axis 35, and its superior iris position can be identified by the fillet 26, for orientation-reference purposes. The optically finished lens element 10, with its axis 36 of astigmatism correction embodied therein, may therefore be assembled at a predetermined prescription angle $\alpha$ of offset in relation to the reference direction along axis 35, for the surgeon's ready reliance in making an accurately oriented intraocular implantation.

The described embodiments of the invention will be seen to meet all stated objects and to demonstrate wide applicability of the invention for a variety of haptic designs and structures, as long as a particular transverse orientation direction inherent in the appearance of the haptic can be recognized by the surgeon as the reference orientation which he will use in his implanting operation and which he will have prescribed as the reference upon which the patient's astigmatism-correction axis of angular offset (in the optically finished lens element 10) has been built into the total implant structure.

It will be understood that for the embodiment of FIG. 1 wherein the lens element 10 is plano-convex, the complex curvature necessary to achieve prescription power and correction is preferably ground into the convex surface of the lens element. However, for all other forms in which a plane side of the lens element 10 is not necessary, the element 10 may be of the double convex or meniscus variety, with one side of the lens element being optically finished with a purely spherical curvature while the directionally corrective feature characterizes the optical finish of the other side of the lens element 10.

While the invention has been described in detail for the preferred forms shown, it will be understood that modifications may be made without departing from the scope of the invention.

What is claimed is:

1. As an article of manufacture, a circular optically finished glass intraocular lens element having a central optical axis and finished with a correction for astigmatism, said correction being at a predetermined transverse orientation through said central axis, and a mounting adapter for said lens element, said adapter being of autoclavable material and in retaining engagement with the periphery of said lens element, said adapter having two diametrically opposed radially outwardly extending foot elements adapted for foot-stabilized positioning of the lens element within a chamber of an eye, said foot elements establishing a recognizably unique transverse axis of orientation of said article through said central axis, and said correction orientation having a predetermined angular relation with respect to said unique axis of orientation.

2. The article of claim 1, in which said adapter is a single piece of said material.

3. The article of claim 1, in which said adapter integrally includes said foot elements in a single piece of said material.

4. The article of claim 2, in which said adapter has a central opening at which said lens element is retained.

5. The article of claim 3, in which said single piece has a central opening of diameter less than the peripheral diameter of said lens element and in lapped circumferential adjacency with one axial side of the periphery of said lens element, and in which said adapter includes at least one further piece of autoclavable material in lapped adjacency with at least part of the other axial side of said periphery and engaged to said single piece within an annulus radially outside but adjacent to said periphery.

6. The article of claim 3, in which said single piece has a central opening of diameter less than the peripheral diameter of said lens element and in lapped circumferential adjacency with one axial side of the periphery of said lens element, and in which said adapter includes at least two further pieces of autoclavable material in lapped adjacency with two angularly spaced parts of the other axial side of said periphery and engaged to said single piece within an annulus radially outside but adjacent to said periphery.

7. The article of claim 5, in which said further piece is annular and has a central opening of diameter less than the peripheral diameter of said lens element.

8. The article of claim 6, in which said further pieces are connected arcuate segments of an annulus having a central opening of diameter less than the peripheral diameter of said lens element.

9. The article of claim 7 or claim 8, in which each said further piece integrally includes at the inner edge of said central opening at least one compliant trans-iris foot formation characterized by an axial-offset portion and a radially outward foot formation integrally connected thereto.

10. The article of claim 5, in which said further piece integrally includes two diametrically opposed radially outwardly extending foot elements.

11. The article of claim 10, in which said last-mentioned foot elements are at locations angularly interposed between said first-mentioned foot elements.

12. As an article of manufacture, a circular optically finished glass intraocular lens element having a central optical axis and finished with a correction for astigmatism, said correction being at a predetermined transverse orientation through said central axis, and a mounting adapter for said lens element, said adapter being of autoclavable material and in retaining engagement with the periphery of said lens element, said adapter having a plurality of angularly spaced radially outwardly extending foot elements adapted for foot-stabilized positioning of the lens element with respect to one or more internal structural features of an eye, said foot elements being characterized to establish a recognizably unique transverse axis of orientation of said article through said central axis, and said correction orientation having a predetermined angular relation with respect to said unique axis of orientation.

13. The article of claim 12, in which at least one of said foot elements is asymmetrically characterized to the exclusion of remaining foot elements, thereby establishing the unique transverse axis.

14. The article of claim 12, in which said lens element is plano-convex and in which said adapter includes a thin glass sheet which is fused to the plane side of said lens element.

15. The article of claim 12, in which said lens element is of finished spherical curvature on one side and is of finished aspherical curvature on the other side.

16. The method of making an intraocular lens which incorporates a prescription angle of astigmatism correction with respect to a predetermined ultimate implanted orientation of the lens in an eye, which comprises selecting a circular optically finished lens element of prescription power and degree of directional correction of astigmatism, selecting haptic structure having a recognizably unique transverse orientation axis which is to have a predetermined orientation when implanted in the eye, and assembling the lens element to the haptic structure at such angular offset of said direction of astigmatism correction with respect to said unique transverse orientation that, upon implantation at said predetermined ultimate implantation orientation, the correct prescription orientation of astigmatism correction is achieved.

* * * * *